(12) United States Patent
Hara et al.

(10) Patent No.: US 7,115,389 B2
(45) Date of Patent: Oct. 3, 2006

(54) METHOD FOR PRODUCING DIPEPTIDE

(75) Inventors: Seiichi Hara, Kanagawa (JP); Kenzo Yokozeki, Kanagawa (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 11/008,203

(22) Filed: Dec. 10, 2004

(65) Prior Publication Data

US 2005/0186654 A1    Aug. 25, 2005

(30) Foreign Application Priority Data

Dec. 11, 2003 (JP) .............................. 2003-413415

(51) Int. Cl.
*C12P 21/06* (2006.01)
(52) U.S. Cl. .............. 435/68.1; 435/252.33; 435/823; 435/849
(58) Field of Classification Search ........ 435/68.1, 435/252.33, 823, 849
See application file for complete search history.

(56) References Cited

U.S. PATENT DOCUMENTS

2005/0037453 A1*  2/2005  Tonouchi et al. .......... 435/68.1

FOREIGN PATENT DOCUMENTS

| EP | 0 278 787 A1 | 8/1988 |
|---|---|---|
| EP | 0 359 399 B1 | 3/1990 |
| JP | 53-92729 | 8/1978 |
| JP | 1-96194 | 4/1989 |
| JP | 6-234715 | 8/1994 |
| WO | WO 90/01555 | 2/1990 |
| WO | WO 04/022733 A1 | 3/2004 |
| WO | PCT/JP2004/010990 | * 2/2005 |
| WO | WO 05/010196 A1 | 2/2005 |

OTHER PUBLICATIONS

S.Akabori, et al., "Protection of Amide-Nitrogen for Peptide Synthesis. A Novel Synthesis of Peptides Containing C-Terminal Glutamine", Bull. Chem. Soc. Jpn, May 1961, p. 739.
Y. Shimonishi, et al., "Studies on the Synthesis of Peptides Containing Glutamine as the C-Terminal. I. Protection of Amide-Nitrogen With Xanthyl Group During Peptide Synthesis", Bull. Chem. Soc. Jpn., vol. 35, No. 12, Dec. 1962, pp. 1966-1970.
Y. Shimonishi, "Studies of the Synthesis of Peptides Containing C-Terminal Glutamine. II. The Synthesis and use of Alpha-Para-Nitrobenzyl Gamma-Methyl L-Glutamate", Bull. Chem. Soc. Jpn., vol. 37, No. 2, Feb. 1964, pp. 200-203.
K.Morihara, et al., "Alpha-Chymotrypsin as the Catalyst for Peptide Synthesis", Biochem. J., (1977), 163, pp. 531-542.
H. Meos, et al., "Single-Step Synthesis of Kyotorphin in Frozen Solutions by Chymotrypsin", Tetrahedron: Asymmetry, vol. 4, No. 7, pp. 1559-1564, 1993, XP-002981749.
V. Tougu, et al., "Peptide Synthesis by Chymotrypsin in Frozen Solutions", FEBS Letters, vol. 329, No. 1-2, pp. 40-42, Aug. 1993, XP-002981750.
J.J. Polderman-Tijmes, et al., "Cloning, Sequence Analysis, and Expression in *Escherichia coli* of the Gene Encoding an Alpha-Amino Acid Ester Hydrolase From Acetobacter Turbidans", Applied and Environmental Microbiology, vol. 68, No. 1, pp. 211-218, Jan. 2002, XP-001121414.

* cited by examiner

*Primary Examiner*—Herbert J. Lilling
(74) *Attorney, Agent, or Firm*—Oblon, Spivak, McClelland, Maier & Neustadt, P.C.

(57) ABSTRACT

A method for producing a dipeptide including the step of exposing a carboxy component and an amine component to an enzyme having an activity to hydrolyze amino acid ester. Such a hydrolase has been found among enzymes in bacteria. The method is useful for producing a peptide simply and inexpensively with a high yield without taking complicate synthetic methods.

16 Claims, No Drawings

SEQUENCE LISTING

```
<160> NUMBER OF SEQ ID NOS: 4

<210> SEQ ID NO 1
<211> LENGTH: 40
<212> TYPE: DNA
<213> ORGANISM: Artificial Sequence
<220> FEATURE:
<223> OTHER INFORMATION: Synthetic DNA

<400> SEQUENCE: 1
gtatcacgag gccctagctg tggtgtcatg gtcggtgatc                           40

<210> SEQ ID NO 2
<211> LENGTH: 40
<212> TYPE: DNA
<213> ORGANISM: Artificial Sequence
<220> FEATURE:
<223> OTHER INFORMATION: Synthetic DNA

<400> SEQUENCE: 2
ttcggggatt ccatatgata ccctttttac gtgaacttgc                           40

<210> SEQ ID NO 3
<211> LENGTH: 35
<212> TYPE: DNA
<213> ORGANISM: Artificial Sequence
<220> FEATURE:
<223> OTHER INFORMATION: Synthetic DNA

<400> SEQUENCE: 3
ccgccgccga ttaatggtgg gacagattac cctttt                              35

<210> SEQ ID NO 4
<211> LENGTH: 36
<212> TYPE: DNA
<213> ORGANISM: Artificial Sequence
<220> FEATURE:
<223> OTHER INFORMATION: Synthetic DNA

<400> SEQUENCE: 4
acccatactg gatccttact gtttcacaac cgggag                              36
```

METHOD FOR PRODUCING DIPEPTIDE

BACKGROUND OF THE INVENTION

1) Field of the Invention

The present invention relates to a method for producing a dipeptide, and particularly relates to a method for producing a peptide simply and inexpensively with a high yield.

2) Description of the Related Art

Peptides have been used in various fields such as pharmaceuticals and foods. For example, L-alanyl-L-glutamine has been widely used as a component of infusion solutions and serum-free media, because it is more stable and more soluble in water than L-glutamine.

As methods for producing the peptides, chemically synthetic methods have been conventionally known, but the methods have not been always simple. Such synthetic methods may include the method using N-benzyloxycarbonyla-lanine (hereinafter referred to as "Z-alanine") and protected L-glutamine [Non-patent Document 1: Bull. Chem. Soc. Jpn., 34, 739 (1961); Non-patent Document 2: Bull. Chem. Soc. Jpn., 35, 1966 (1962)], the method using Z-alanine and protected L-glutamic acid-γ-methyl ester [Non-patent Document 3: Bull. Chem. Soc. Jpn., 37, 200)1964)], the method using Z-alanine ester and unprotected glutamic acid (Patent Document 1: JP 1-96194 A), the method of generating an N-(2-substituted)-propionyl glutamate derivative as an intermediate using 2-substituted propionyl halide as a raw material.

However, in any of the methods, introduction/elimination of a protecting group or the use of an optically active intermediate is required. Thus none of these production methods are industrially advantageous and satisfactory.

Meanwhile, typical methods for producing peptides using enzymes may include a condensation reaction using an N-protected and C-unprotected carboxy component and an N-unprotected and C-protected amine component (Reaction 1), and a substitution reaction using an N-protected and C-protected carboxy component and an N-unprotected and C-protected amine component (Reaction 2). Examples of the Reaction 1 may include the method for producing Z-aspartyl-phenylalanine methyl ester from Z-aspartic acid and phenylalanine methyl ester (Patent Document 3: JP 53-92729 A), and examples of the Reaction 2 may include the method for producing acetyl-phenylalanyl-leucineamide from acetyl phenylalanine ethyl ester and leucineamide [Non-patent Document: Biochemical J., 163, 531 (1977)]. There are extremely few reports of the method using the N-unprotected and C-protected carboxy component. An example of a substitution reaction using an N-unprotected and C-protected carboxy component and an N-unprotected and C-protected amine component (Reaction 3) may be found in WO 90/01555 (Patent Document 4), and may include the method for producing arginyl-leucineamide from arginine ethyl ester and leucineamide. Examples of a substitution reaction using an N-unprotected and C-protected carboxy component and an N-unprotected and C-unprotected amine component (Reaction 4) may be found in EP 278787A1 (Patent Document 5) and EP 359399B1 (Patent Document 6), and may include the method for producing tyrosyl alanine from tyrosine ethyl ester and alanine.

The most inexpensive method of production among the above Reaction 1 to Reaction 4 may obviously be reactions categorized in Reaction 4 with the least protecting groups.

However, the prior-art example of the Reaction 4 (in Patent EP 278787A1) has the following crucial problems:

(1) Extremely slow peptide-synthesizing rate; (2) Low peptide generation yield; (3) Limitation of the producible peptides to those having relatively high hydrophobicity; (4) Requirement of a large amount of enzymes to be added; and (5) Requirement of a relatively expensive carboxy peptidase preparation derived from fungi, yeasts and plants.

Among the methods falling into the category of the Reaction 4, none of known methods use enzymes derived from bacteria and yeasts other than *Saccharomyces,* and none of known methods can produce highly hydrophilic peptides such as alanyl-glutamine. In such a situation, development of the industrially inexpensive methods for producing these peptides has been desired.

SUMMARY OF THE INVENTION

It is an object of the present invention to provide a novel enzyme which can be used for producing peptides simply and inexpensively with a high yield without working through complex synthetic routes. More particularly, it is the object to provide a new enzyme which catalyzes a peptide synthesis reaction from a carboxy component and an amine component, a microorganism which produces this enzyme and an inexpensive method for producing the peptides using this enzyme or the microorganism.

As a result of an intensive study in the light of the above object, the present inventors have newly found an enzyme having an activity to hydrolyze amino acid ester and efficiently catalyzing a production of a peptide in a bacterium belonging to genus *Acetobacter.* Furthermore, the present inventors have found out that the above object is accomplished by using this enzyme, and thereby completed the present invention. As used herein, the enzyme having the activity to hydrolyze the amino acid ester is also referred to as "amino acid ester hydrolase", and the activity of the enzyme is referred to as "amino acid ester hydrolase activity".

The amino acid ester hydrolase is an enzyme catalyzing a specific hydrolysis. The specific hydrolysis catalyzes the reaction represented by the following general formula 1.

$$A\text{-}B + H_2O \rightarrow A\text{-}OH + B\text{—}H \tag{1}$$

wherein "A-B" indicates a compound made by binding a substance "A" with a substance "B".)

In the prior art, it has not been known at all that there is an amino acid ester hydrolase having an activity which also facilitates a reaction to synthesize a peptide from a carboxy component and an amine component.

The invention is as follows.

[1] A method for producing a dipeptide comprising the step of exposing a carboxy component and an amine component to an enzyme having an activity to hydrolyze amino acid ester.

[2] The method for producing the dipeptide according to [1] above, wherein the enzyme is derived from one or more selected from the group consisting of a culture of a microorganism producing an enzyme having an activity to hydrolyze amino acid ester, microbial cells separated from the culture, and a treated microbial cell product.

[3] The method for producing the dipeptide according to [2] above, wherein the microorganism producing the enzyme having the activity to hydrolyze the amino acid ester is a transformant capable of expressing the enzyme to hydrolyze the amino acid ester.

[4] The method for producing the dipeptide according to any one of [1] to [3] above, wherein the carboxy component is L-alanine methyl ester.

[5] The method for producing the dipeptide according to any one of [1] to [4] above, wherein the amine component is L-glutamine.

The present invention provides the novel enzyme by which complicate synthetic processes such as introduction and elimination of protecting groups may be simplified, and which can be used for producing the peptide simply and inexpensively with a high yield. With this enzyme, the efficient method for producing the peptides is provided.

These and other objects, features and advantages of the present invention are specifically set forth in or will become apparent from the following detailed descriptions of the invention.

DETAILED DESCRIPTIONS

The embodiments of the present invention will be illustrated in detail in the order of (1) a microorganism which produces an enzyme used in the production method of the invention, (2) cultivation of the microorganisms, (3) purification of the enzyme, (4) method for producing a dipeptide, (5) isolation of DNA encoding a protein having a peptide-synthesizing activity, and the like.

(1) Microorganism Which Produces Enzyme Used for the Production Method of the Present Invention The enzyme used in the invention may be a protein having the amino acid ester hydrolase activity and having an ability to generate a peptide from a carboxy component and an amine component. The microorganisms which produce such an enzyme are not particularly limited. As used herein, the carboxy component refers to a component which supplies a carbonyl (CO) site in a peptide bond (—CONH—), and the amine component refers to a component which supplies an amino (NH) site in the peptide bond. Also as used herein, a "peptide" refers to a polymer having at least one peptide bond unless otherwise indicated. Also as used herein, a "dipeptide" refers to a peptide having one peptide bond.

The microorganisms which produce the enzyme used in the invention may include, for example, bacteria belonging to the genus *Acetobacter* and the like, and more specifically *Acetobacter pasteureanus* ATCC 9325 strain, and the like. Bacterial strains to which ATCC numbers are allotted are those deposited at American Type Culture Collection (P. O. box 1549, Manassas, Va. 20110, USA), and may be furnished by enquiring the number.

The enzyme used in the invention may be isolated from microbial cells of the bacterium belonging to the genus *Acetobacter* as mentioned above, and the isolated enzyme may further be purified. Using genetic engineering techniques with the isolated enzyme, it may also be possible to obtain the enzyme of the invention and the microorganism which produces the enzyme. That is, DNA encoding the enzyme of the invention may be isolated based on the isolated and purified enzyme, which may then be introduced into an appropriate host and expressed, for obtaining the enzyme and the microorganism of the present invention. Alternatively, probes may be produced based on the polynucleotide encoding the enzyme of the invention obtained from *Acetobacter pasteureanus* and the like, with which an enzyme having the ability to synthesize the peptide from the carboxy component and the amine component may be obtained from other microorganisms. Various gene recombination techniques are described in Molecular Cloning, 2nd edition, Cold Spring Harbor Press (1989) and the like.

(2) Cultivation of Microorganism

Cultured microbial cells of a microorganism which produces the enzyme of the invention may be produced merely by culturing the microorganism in an appropriate medium. The medium therefor is not particularly limited so long as the microorganism can grow in it, and may be an ordinary medium comprising ordinary sources of carbon, nitrogen phosphorus, sulfur, inorganic ions and, if necessary, organic nutrition sources.

Any carbon source may be employed as long as it can be utilized by the above microorganism, and specific examples thereof may include sugars such as glucose, fructose, maltose and amylose, alcohols such as sorbitol, ethanol and glycerol, organic acids such as fumaric acid, citric acid, acetic acid and propionic acid and salts thereof, and hydrocarbons such as paraffin, as well as mixtures thereof.

Examples of the nitrogen source may include ammonium salts of inorganic acids such as ammonium sulfate and ammonium chloride, ammonium salts of organic acids such as ammonium fumarate and ammonium citrate, nitrate such as sodium nitrate and potassium nitrate, organic nitrogen compounds such as peptone, yeast extract, meat extract and corn steep liquor, and mixtures thereof.

Additionally, the medium may appropriately contain any nutrition sources that are contained in an ordinary medium, such as inorganic salts, trace metal salts and vitamins.

Conditions for the cultivation are not particularly limited. For example, the cultivation may be performed under an aerobic condition with appropriately controlling pH and temperature in the range of the pH of 5 to 8 and the temperature of 15 to 40° C. for about 12 to 48 hours.

(3) Purification of Enzyme

An example of the method for isolating or purifying the protein having the amino acid ester hydrolase activity and having the ability to synthesize the peptide will be illustrated. First, the microorganism which produces the protein having the amino acid ester hydrolase activity and having the ability to generate the peptide is cultured. The cultured microbial cells thus obtained are then disrupted by a physical method such as ultrasonic disruption or an enzymatic method using a cell wall dissolving enzyme, and the insoluble fraction therein is removed by centrifugation and the like, to prepare a microbial cell extract solution.

The fraction containing the cell extract solution may be separated by a combination of usual methods for the protein purification, such as anion exchange chromatography, cation exchange chromatography and gel filtration chromatography, to purify the protein having the aforementioned specific ability.

Carriers for the anion exchange chromatography may include, for example, Q-Sepharose HP (supplied from Amersham). Carriers for the cation exchange chromatography may include, for example, Mono S HR (supplied from Amersham). The extract solution may be passed through a column that has been filled with a carrier such as the above whereby an objective protein may be absorbed to the column. The column may then be washed, and subsequently the objective protein may be eluted using a buffer with high salt concentration. For the elution, the salt concentration may be increased stepwise or in a gradient manner.

The protein purified as the above may further be purified uniformly by gel filtration chromatography and the like. Carriers for the gel filtration chromatography may include Sephadex 200 pg (supplied from Amersham) and the like.

In the above purification, a fraction containing the enzyme used in the invention may be identified by measuring a peptide-synthesizing activity in each fraction by the methods that will be discussed below.

(4) Method for Producing Dipeptide

In the method for producing a dipeptide of the invention, the carboxy component and the amine component are exposed to the enzyme having the activity to hydrolyze amino acid ester. That is, in the method for producing the dipeptide of the invention, the dipeptide is produced from the carboxy component and the amine component using the enzyme and/or an enzyme-containing substance which hydrolyzes the amino acid ester.

The exposure of the enzyme or the enzyme-containing substance used for the invention to the carboxy component and the amine component may be achieved by merely mixing the enzyme or the enzyme-containing substance, the carboxy component and the amine component. More specifically, the enzyme or the enzyme-containing substance may be added to a solution containing the carboxy component and the amine component, to perform a reaction. When using a microorganism which produces the enzyme, the exposure may be achieved by culturing the microorganism which produces the enzyme, to produce and accumulate the enzyme in the microorganism itself or in culture broth of the microorganism, and then adding the carboxy component and the amine component thereto. The dipeptide thus synthesized may be recovered and if necessary purified by standard methods. Two or more forms of the above enzyme or the enzyme-containing substance may be combined for use.

The "enzyme-containing substance" may be those containing the enzyme, and specific forms thereof may include cultured products of the microorganism which produces the enzyme, microbial cells separated from the cultured products, and a treated product obtained by treating the microbial cells, and the like. The cultured product is a product obtained by culturing the microorganism, and more specifically, refers to a mixture of the microbial cells, a medium used for culturing the microorganism and substances produced by the cultured microorganism, and the like. The microbial cells may also be washed and used as washed microbial cells. The treated product of microbial cells may include those where the microbial cells are disrupted, lysed and freeze-dried, and may further include a crude enzyme collected by treating the microbial cells, and a purified enzyme obtained by purification thereof. The purified enzyme to be used may include partially purified enzymes obtained by various purification methods, and immobilized enzymes which are immobilized by a covalent bond method, an absorption method, an entrapping method and the like. Depending on the microorganism to be used, microorganisms may be partially lysed during the cultivation. In this case, the supernatant of the cultured liquid may also be utilized as the enzyme-containing substance.

As the microorganism containing the enzyme, a wild strain may be used. Alternatively, a genetic recombinant strain which expresses the present enzyme may also be used. As the microorganism, without limiting to the enzyme-producing microbial cells themselves, the treated cells of the microorganism such as microbial cells treated with acetone and lyophilized microbial cells may be used. Immobilized microbial cells immobilized by the covalent bond method, the absorption method, the entrapping method and the like may also be used. The immobilized microbial cells that have been further subjected to other treatments may also be used.

In most of cases, the cultured products, the cultured microbial cells or the treated microbial cells may also contain enzymes which are not involved in peptide production and degrade produced peptides. In this case, it is sometimes preferable to add a metal protease inhibitor such as ethylenediamine tetraacetatic acid (EDTA). The amount of such an inhibitor to be added may be in the range of 0.1 mM to 300 mM, and preferably from 1 mM to 100 mM.

The amount of the enzyme or the enzyme-containing substance to be used may be in a range of an amount (effective amount) by which an objective effect is exerted. This effective amount may be easily obtained by a simple preliminary experiment by those skilled in the art. In the case of using the enzyme itself, the amount may be from about 0.01 to 100 units (U). In the case of using the washed microbial cells, the amount may be from about 1 to 500 g/L.

The carboxy component is not particularly limited so long as the component can form a peptide by condensing with the amine component, i.e., another substrate. The carboxy component may include, for example, L-alanine methyl ester and the like.

The amine component is not particularly limited so long as the component can form a peptide by condensing with the carboxy component, i.e., another substrate. The amine component may include, for example, L-glutamine and the like.

Concentrations of the carboxy and amine components which are starting raw materials may be each from 1 mM to 10 M, and preferably from 0.05 M to 2 M. In some cases, it is preferable to add the amine component at an amount equal to or more than the carboxy component. In the case where the high concentration of the substrate may inhibit the reaction, the substrate may be added sequentially to the reaction in order to keep the low concentration of the substrate so as not to inhibit the reaction.

The peptide may be produced at reaction temperature of 0 to 60° C., and preferably of 5 to 40° C. The peptide may be produced at reaction pH of 6.5 to 10.5, and preferably of 7.0 to 10.0.

(5) Isolation of DNA Encoding Protein having Peptide-synthesizing Activity

[5-1] Isolation of DNA

The microorganism used in the present invention has an ability to produce a dipeptide from the amino acid ester and the amino acid. That is, with genetic engineering techniques, DNA encoding the protein which is capable of synthesizing the dipeptide from the amino acid ester and the amino acid may be isolated from the microorganisms such as those mentioned above, and a transformant may be produced with the isolated DNA, whereby the protein (peptide synthesizing enzyme) which synthesizes the dipeptide from the amino acid ester and the amino acid may be obtained. As an example, an embodiment of the method for isolating DNA encoding a protein which synthesizes a dipeptide from an L-amino acid ester and an L-amino acid from a microorganism, and making a transformant with the DNA will be illustrated.

First, a purified enzyme is obtained from the above microorganism as illustrated in the above (3), and an amino acid sequence of the purified peptide-synthesizing enzyme is determined. The amino acid sequence may be determined using Edman's method [Edman, P., Acta Chem. Scand., 4, 227 (1950)]. The amino acid sequence may also be determined using a sequencer supplied from Applied Biosystems. For the purified peptide-synthesizing enzyme, 30 residues of the amino acid sequence from an N-terminus may be determined. Based on the determined amino acid sequence, a nucleotide sequence of DNA encoding the amino acid sequence may be deduced. In order to deduce the nucleotide sequence of the DNA, universal codons may be employed.

Based on the deduced nucleotide sequence, a DNA molecule of about 30 base pairs is synthesized. The method for synthesizing the DNA molecule is disclosed in Tetrahedron Letters, 22, 1859 (1981). The DNA molecule may also be synthesized using a synthesizer supplied from Applied Biosystems. The DNA molecule may be utilized as a probe when full length of DNA encoding the peptide-synthesizing enzyme is isolated from a chromosomal gene library of microbial cells. Alternatively, the DNA molecule may also be utilized as a primer when the DNA encoding the peptide-synthesizing enzyme is amplified by a PCR method. But, the DNA amplified using the PCR method does not include the full length of DNA encoding the peptide-synthesizing enzyme. Thus, using the DNA amplified using the PCR method as a probe, the full length DNA encoding the peptide-synthesizing enzyme may be isolated from the chromosomal gene library of the microorganism.

Manipulation of the PCR method is described in White Y. J. et al., Trends Genet., 5, 185 (1989), and the like. Methods for preparing chromosomal DNA and further methods for isolating an objective DNA molecule from a gene library using a DNA molecule as a probe are described in Molecular Cloning, 2nd edition, Cold Spring Harbor Press (1989) and the like.

Methods for determining a nucleotide sequence of DNA encoding the isolated peptide-synthesizing enzyme are described in A Practical Guide to Molecular Cloning, John Wiley & Sons, Inc., (1986). Also, the nucleotide sequence may be determined using the DNA sequencer supplied from Applied Biosystems.

The DNA which may be used in the invention are not only the DNA obtained as the above. Even DNA obtained by artificially giving mutations to the DNA encoding the peptide-synthesizing enzyme isolated from chromosomal DNA of the certain microbial cells may also be available as the DNA in the present invention as long as it encodes the peptide-synthesizing enzyme. Frequently used methods for artificially giving mutations may include site-directed mutagenesis methods described in Method. in Enzymol., 154 (1987).

Furthermore, the DNA which may be used in the present invention also includes DNA having a nucleotide sequence which hybridizes under a stringent condition with a polynucleotide (DNA or RNA) having a nucleotide sequence complementary to a nucleotide sequence of the DNA isolated from the chromosomal DNA and the like in the aforementioned manner and encoding the protein having the peptide-synthesizing enzyme activity.

As used herein, the "stringent condition" refers to the condition where a so-called specific hybrid is formed whereas no non-specific hybrid is formed. Although it is difficult to clearly quantify this condition, examples thereof may include the condition where a pair of DNA sequences with high homology, e.g., DNA sequences having the homology of 50% or more, more preferably 80% or more, and still more preferably 90% or more are hybridized whereas DNA with lower homology than that are not hybridized, and a washing condition of an ordinary Southern hybridization, i.e., hybridization at salt concentrations equivalent to 1×SSC and 0.1% SDS at 60° C., preferably 0.1×SSC and 0.1% SDS at 60° C., and more preferably 0.1×SSC and 0.1 SDS at 65° C. The activity of the peptide-synthesizing enzyme is as already illustrated as the above. But, in the case of the nucleotide sequence which hybridizes with the complementary nucleotide sequence under the stringent condition, it is desirable that the enzyme derived from the sequence retains the enzyme activity at about a half or more, more preferably 80% or more, and still preferably 90% or more of the protein having the original amino acid sequence under the condition at 50° C. at pH 8.

Furthermore, a protein which is substantially identical to the protein encoded by the isolated DNA may also be used in the present invention. Therefore, DNA encoding a protein having an amino acid sequence including one or several amino acid substitutions, deletions, insertions, additions and/or inversions in the amino acid sequence encoded by the isolated DNA, and having the peptide-synthesizing enzyme activity which catalyzes the reaction from L-amino acid ester and L-amino acid to the dipeptide may also be used in the present invention. As used herein, "several amino acids" are in the range where a three-dimentional structure of the protein with amino acid residues and the peptide-synthesizing enzyme activity are not significantly impaired, and specifically from 2 to 50, preferably 2 to 30, and more preferably 2 to 10 amino acids. The activity of the peptide-synthesizing enzyme is as already illustrated. But, in the case of the amino acid sequence including one or several amino acid substitutions, deletions, insertions, additions and/or inversions therein, it is desirable that the enzyme derived from the sequence retains the enzyme activity at about a half or more, more preferably 80% or more, and still preferably 90% or more of the protein having the original amino acid sequence under the condition at 50° C. at pH 8.

In the case of isolating the DNA from the microorganism in the aforementioned manner, the following DNA may suitably be used in the present invention. As an example, one of the specified nucleotide sequence of the isolated DNA is referred to as the nucleotide sequence y, and an amino acid sequence encoded by this nucleotide sequence is referred to as the amino acid sequence Y.

(i) DNA comprising the nucleotide sequence y.

(ii) DNA which hybridizes with a polynucleotide comprising a nucleotide sequence complementary to the nucleotide sequence y under the stringent condition and encodes a protein having the peptide-synthesizing enzyme activity which catalyzes the reaction from L-amino acid ester and L-amino acid to the dipeptide.

(iii) DNA encoding a protein having the amino acid sequence Y.

(iv) DNA encoding a protein having an amino acid sequence including one or several amino acid substitutions, deletions, insertions, additions and/or inversions in the amino acid sequence Y, and encodes a protein having the peptide-synthesizing enzyme activity which catalyzes the reaction of L-amino acid ester and L-amino acid to generate the dipeptide.

[5-2] Production of Transformants

Subsequently, production of transformants which express the protein having the peptide-synthesizing enzyme activity will be illustrated. There has been reported numerous examples for producing useful proteins such as enzymes and physiologically active substances by taking advantage of recombinant DNA technology. By the use of the recombinant DNA technology, it is possible to perform mass production of the useful protein which naturally present in a trace amount.

Suitable transformants which may be used in the invention may include, for example, transformants capable of expressing proteins such as the following (A), (B) and (C).

(A) A protein having the amino acid sequence Y.

(B) A protein having an amino acid sequence including one or several amino acid substitutions, deletions, insertions, additions and/or inversions in the amino acid sequence Y, and having the peptide-synthesizing enzyme activity which catalyzes the reaction from L-amino acid ester and L-amino acid to the dipeptide.

(C) A protein encoded by DNA which hybridizes with a polynucleotide comprising a nucleotide sequence complementary to the nucleotide sequence y under the stringent condition and encodes a protein having the peptide-synthesizing enzyme activity which catalyzes the reaction of L-amino acid ester and L-amino acid to produce the dipeptide.

The transformants which express the proteins having the peptide-synthesizing enzyme activity of the above (A) to (C) may be produced by introducing the DNA sequences of (i) to (iv) shown above [5-1] into host cells. That is, the DNA sequences of (i), (ii), (iii) or (iv) may be incorporated in an expression vector capable of performing expression in the host cells, which is then introduced into the host cells.

The mutants shown in the above (B) may be obtained by modifying the nucleotide sequence such that an amino acid at specific position of the present enzyme gene is substituted, deleted, inserted or added. Such a mutation may be caused by the site-directed mutagenesis. The modified DNA such as those mentioned above may also be obtained by mutagenesis that are known in the prior art. Examples of the mutagenesis may include a method of treating the DNA encoding the present enzyme with hydroxylamine and the like in vitro, and a method of treating bacteria of genus Escherichia carrying the DNA encoding the present enzyme with a mutagenic agent such as ultraviolet ray or N-methyl-N'-nitro-N-nitrosoguanidine (NTG) or nitrous acid which is usually used for artificial mutagenesis.

In the case of producing a protein on a large scale using the recombinant DNA technology, a preferable mode thereof may include formation of an inclusion body of the protein. The inclusion body is configured by aggregation of the protein in the protein-producing transformant. The advantages of this expression production method may include the protection of the objective protein from digestion by proteases present in the microbial cells, and ready purification of the objective protein that may be performed by disruption of the microbial cells and the following centrifugation.

The protein inclusion body obtained in this way may be solubilized by a protein denatureing agent, which is then subjected to activation regeneration mainly by eliminating the denaturing agent, to be converted into the correctly refolded and physiologically active protein. There are many examples of such procedures, such as activity regeneration of human interleukin 2 (JP 61-257931 A).

To obtain the active protein from the protein inclusion body, a series of the manipulations such as solubilization and activity regeneration is required, and thus the manipulations is more complicate than those in the case of directly producing the active protein. However, when a protein which affects microbial cell growth is produced on a large scale in the microbial cells, effects thereof may be inhibited by accumulating the protein as the inactive inclusion body in the microbial cells.

The methods for producing the objective protein on a large scale as the inclusion body may include methods of expressing the protein alone under control of a strong promoter, as well as methods of expressing the objective protein as a fusion protein with a protein known to be expressed in a large amount.

It is effective to arrange a recognition sequence of restriction protease at an appropriate position, for cleaving out the objective protein after the expression of the fusion protein.

When the protein is produced on a large scale using the recombinant DNA technology, the host cells to be transformed may include bacterial cells, actinomycetal cells, yeast cells, fungal cells, plant cells and animal cells. In general, intestinal bacteria such as Escherichia coli, preferably Escherichia coli are preferred, since there are many findings for technology to produce the protein on a large scale using the intestinal bacteria such as Escherichia coli. One mode of methods for producing the peptide-synthesizing enzyme using transformed Escherichia coli will be illustrated hereinbelow.

As promoters which express the DNA encoding the peptide-synthesizing enzyme, it is possible to use the promoters usually used for production of foreign proteins in Escherichia coli. Example thereof may include strong promoters such as T7 promoter, lac promoter, trp promoter, trc promoter, tac promoter, and $P_R$ and $P_L$ promoters of lambda phage.

Production of the peptide-synthesizing enzyme incorporated in a fusion protein inclusion body may be achieved by ligating a gene encoding other protein, preferably a hydrophilic peptide to an upstream or downstream of the peptide-synthesizing enzyme gene, whereby a fusion protein gene may be produced. Such a gene encoding the other protein may be the one which increases an accumulation amount of the fusion protein and enhances solubility of the fusion protein after steps of modification and regeneration, and example thereof may include T7 gene 10, β-galactosidase gene, dehydrofolate reductase gene, interferon γ gene, interleukin-2 gene, prochymosin gene and the like as candidates.

Ligation of these genes to the gene encoding the peptide-synthesizing enzyme may be performed so that reading frames of codons are matched. Such a ligation may be performed by ligation at an appropriate restriction enzyme site, or by utilization of synthetic DNA with appropriate sequence.

In order to augment a production amount, it is sometimes preferable to ligate a terminator, i.e., a transcription termination sequence to the downstream of the fusion protein gene. This terminator may include T7 terminator, fd phage terminator, T4 terminator, terminator of tetracycline resistant gene, terminator of Escherichia coli trpA gene, and the like.

As a vector to introduce the gene encoding the peptide-synthesizing enzyme or the fusion protein of the peptide-synthesizing enzyme and the other protein into Escherichia coli, so-called multiple copying types are preferable. Preferable plasmids may be those having a replication origin derived from ColE1, such as pUC type plasmids, pBR322 type plasmids or derivatives thereof. As used herein, the "derivatives" may include those in which modification is given to the plasmids by substitution, deletion, insertion, addition and/or inversion of nucleotides. The modification as referred to herein may also include modification by mutagenic treatments by mutagenic agents and UV irradiation or natural mutation. More specifically, examples of the vectors for use may include pUC19, pUC18, pBR322, pHSG299, pHSG298, pHSG399, pHSG398, RSF1010, pMW119, pMW118, pMW219, pMW218, and the like. The vectors for use may also include phage DNA and transposon DNA.

It is preferred that the vector has a marker such as ampicillin resistant gene for facilitating selection of the transformant. As such a plasmid, expression vectors carrying strong promoters are commercially available (pUC types (supplied from Takara Shuzo Co., Ltd.), pPRO types (supplied from Clontech), pKK233-2 (supplied from Clontech) and the like).

Recombinant DNA may be obtained by ligating the promoter, the gene encoding the peptide-synthesizing enzyme or the fusion protein of the peptide-synthesizing enzyme and the other protein and the terminator in this order to obtain a fragment, and further ligating the resulting fragment to the vector DNA.

Using the resulting recombinant DNA, transformation of, e.g., *Escherichia coli* may be performed. Cultivation of this *Escherichia coli* may result in expression and production of the peptide-synthesizing enzyme or the fusion protein of the peptide-synthesizing enzyme and the other protein. The host to be transformed may be strains that are usually employed for the expression of foreign genes. Preferable examples thereof may include *Escherichia coli* JM109 strain. Methods for performing transformation and methods of selecting the transformant are described in Molecular Cloning, 2nd edition, Cold Spring Harbor Press (1989) and the like.

In the case of expressing the enzyme as a part of the fusion protein, the fusion protein may be composed so as to be able to cleave the peptide-synthesizing enzyme therefrom using a restriction protease which recognizes a sequence of blood coagulation factor Xa, kallikrein or the like which is not present in the peptide-synthesizing enzyme.

The production media to be used may include the media usually used for culturing *Escherichia coli,* such as M9-casamino acid medium and LB medium. Culture conditions and production induction conditions may be appropriately selected depending on types of the vector marker, the promoter, the host bacterium and the like.

The peptide-synthesizing enzyme or the fusion protein of the peptide-synthesizing enzyme and the other protein may be recovered by the following method: when the peptide-synthesizing enzyme or the fusion protein of the peptide-synthesizing enzyme is solubilized in the microbial cells, the microbial cells may be collected and then disrupted or lysed, to obtain a crude enzyme solution. If necessary, the peptide-synthesizing enzyme or the fusion protein may further be subjected to purification in accordance with ordinary methods such as precipitation, filtration and column chromatography. The purification may also be performed in accordance with methods utilizing an antibody against the peptide-synthesizing enzyme or the fusion protein.

In the case where the protein inclusion body is formed, this may be solubilized with a denaturing agent. The inclusion body may be solubilized together with the microbial cells. However, considering the following purification process, it is preferable to remove the inclusion body before solubilization. Collection of the inclusion body from the microbial cells may be performed in accordance with conventionally and publicly known methods. For example, the microbial cells are broken, and the inclusion body is collected by centrifugation and the like. The denaturing agent which solubilizes the protein inclusion body may include guanidine-hydrochloric acid (e.g., 6 M, pH 5 to 8), urea (e.g., 8 M), and the like.

As a result of removal of the denaturing agent by dialysis and the like, the protein may be regenerated as having the activity. Dialysis solutions used for the dialysis may include tris hydrochloric acid buffer, phosphate buffer and the like. The concentration thereof may be 20 mM to 0.5 M, and pH thereof may be 5 to 8.

It is preferred to keep that the protein concentration at a regeneration step is kept at about 500 µg/ml or less. In order to inhibit self-crosslinking of the regenerated peptide-synthesizing enzyme, it is preferred that dialysis temperature is kept at 5° C. or below. Methods for removing the denaturing agent other than the dialysis method may include a dilution method and an ultrafiltration method. The regeneration of the activity is anticipated by using any of these methods.

Gene engineering techniques may be carried out in accordance with the techniques described in references such as Molecular Cloning, 2nd edition, Cold Spring Harbor Press (1989) and the like.

EXAMPLES

The present invention will be illustrated in more detail with reference to the following Examples, but the invention is not limited thereto. Products were identified in accordance with a ninhydrin color reaction on thin layer chromatogram (qualitative), and quantified by the below-mentioned high performance liquid chromatography:

Column: InertsiL ODS-2 (supplied from GL Science), eluent: phosphoric acid aqueous solution containing 5.0 mM sodium 1-octanesulfonate (pH 2.1): methanol=100:15 to 50, flow rate: 1.0 mL/min, and detection: 210 nm.

1. Expression of amino acid ester hydrolase derived from *Acetobacter pasteureanus* ATCC 9325 in *E. coli*

A medium containing 50 g of glucose, 5 g of ammonium sulfate, 1 g of monopotassium phosphate, 3 g of dipotassium phosphate, 0.5 g of magnesium sulfate, 5 g of yeast extract, 5 g of peptone in 1 L (pH 7.0) was prepared, and 50 mL of the medium was dispensed into a 500 mL Sakaguchi flask, and sterilized at 115° C. for 15 min. The medium was then inoculated with one loopful of *Acetobacter pasteureanus* ATCC 9325 strain that had been cultured at 30° C. for 16 hours in the same medium. The inoculated medium was then cultured with shaking at 30° C. at 120 reciprocations/min for 16 hours.

Then, 50 mL of cultured medium was centrifuged (12000 rpm, 4° C., 15 min), and cells were collected. Chromosomal DNA was obtained from these cells using QIAGEN Genomic-tip System (Qiagen) in accordance with the procedure described in the instructions thereof.

A promoter region of trp operon on chromosomal DNA of *Escherichia coli* W3110 was amplified as an objective gene region by PCR using oligonucleotides shown in SEQ ID NOS:1 and 2 as primers, and the resulting DNA fragment was ligated to pGEM_Teasy vector (supplied from Promega). *E. coli* JM109 was transformed with this solution containing the ligated product, and a strain having an objective plasmid where the trp promoter was inserted in an opposite direction to the lac promoter was selected in ampicillin resistant strains. Subsequently, the plasmid was treated with EcoO109I/EcoRI, and the DNA fragment obtained thereby containing the trp promoter was ligated to pUC 19 (supplied from Takara) that had been treated with EcoO109I/EcoRI. The *Escherichia coli* JM109 was transformed with this solution containing the ligated product, and a strain having the plasmid having a trp promoter region was selected in ampicillin resistant strains. Subsequently, a DNA fragment obtained by treating this plasmid with HindIII/PvuII was ligated to a DNA fragment containing rrnB terminator that had been obtained by treating pKK223-3 (supplied from Amersham Pharmacia) with HindIII/HincII. The *E. coli* JM109 was transformed with this solution containing the ligated product, and a strain having the plasmid having the trp promoter region and containing the rrnB terminator was selected in the ampicillin resistant strains. This plasmid was designated as pTrpT.

Using chromosomal DNA from the *Acetobacter pasteureanus* ATCC 9325 strain as a template, an objective gene containing an amino acid ester hydrolase gene was amplified by PCR employing oligonucleotides shown in the above SEQ ID NOS: 3 and 4 as the primers. This DNA fragment was treated with AseI/BamHI, and the resulting DNA fragment was ligated to pTrpT that had been treated with NdeI/BamHI. The *Escherichia coli* JM109 was transformed with this solution containing the ligated product, and a strain having the plasmid containing a nucleotide sequence encoding the protein which express the amino acid ester hydrolase was selected in ampicillin resistant strains. This plasmid was designated as pTrpT_Ap_aehA.

3 ml of the medium (2 g/L of glucose, 10 g/L of yeast extract, 10 g/L of casamino acid, 5 g/L of ammonium sulfate, 3 g/L of potassium dihydrogen phosphate, 1 g/L of dipotassium hydrogen phosphate, 0.5 g/L of magnesium phosphate heptahydrate, and 100 mg/L of ampicillin) in a standard test tube was inoculated with one loopful of *Eschericia coli* JM109 having plasmid pTrpT_Ap_aehA, and mass cultivation was performed at 25° C. for 20 hours. When cultured with L-alanine methyl ester and L-glutamine that had been added thereto, a cultured solution exhibited L-alanyl-L-glutamine synthesizing activity at 0.02 U per mL, and thus it was confirmed that α-amino acid ester hydrolase had the peptide-synthesizing activity. No activity was detected with the control transformant into which pTrpT alone was introduced.

INDUSTRIAL APPLICABILITY

The invention is highly useful in industrial peptide production.

Although the present invention has been described with reference to the preferred examples, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims along with their full scope of equivalents.

What is claimed is:

1. A method for producing a dipeptide comprising contacting a carboxy component and an amine component to an enzyme having an activity to hydrolyze amino acid ester or enzyme-containing substance having an activity to hydrolyze amino acid ester, wherein said enzyme or enzyme-containing substance is derived from a microorganism belonging to the genus *Acetobacter*.

2. The method for producing the dipeptide according to claim 1 wherein the enzyme or enzyme-containing substance is derived from one or more selected from the group consisting of a culture of a microorganism producing an enzyme having an activity to hydrolyze amino acid ester, microbial cells separated from the culture, and a treated microbial cell product.

3. The method for producing the dipeptide according to claim 2 wherein the microorganism producing the enzyme having the activity to hydrolyze amino acid ester is a transformant capable of expressing the enzyme to hydrolyze the amino acid ester.

4. The method for producing the dipeptide according to claim 1 wherein the carboxy component is L-alanine methyl ester.

5. The method for producing the dipeptide according to claim 1 wherein the amine component is L-glutamine.

6. The method for producing the dipeptide according to claim 1 wherein the microorganism is an *Acetobacterpasteureanus*.

7. The method for producing the dipeptide according to claim 1 wherein the microorganism is *Acetobacter pasteureanus* ATCC 9325 strain.

8. The method for producing the dipeptide according to claim 1, wherein said method comprises culturing a microorganism containing a gene encoding said enzyme in a suitable medium and under suitable conditions to express said enzyme, wherein said contacting occurs in said medium, and wherein said microorganism containing a gene encoding said enzyme is of the genus *Acetobacter*.

9. The method for producing the dipeptide according to claim 1, wherein said method comprises culturing a microorganism containing a gene encoding said enzyme in a suitable medium and under suitable conditions to express said enzyme, isolating the microorganism from said medium, and said contacting occurs with the isolated microorganism, wherein said microorganism containing a gene encoding said enzyme is of the genus *Acetobacter*.

10. The method for producing the dipeptide according to claim 1, wherein said method comprises culturing a microorganism containing a gene encoding said enzyme in a suitable medium and under suitable conditions to express said enzyme, isolating the microorganism from said medium, treating said microorganism by a method selected from the group consisting of disruption, lysing, and freeze-drying to produce a treated microorganism cell product, and said contacting occurs with the treated microorganism cell product, and wherein said microorganism containing a gene encoding said enzyme is of the genus *Acetobacter*.

11. The method for producing the dipeptide according to claim 1, wherein said method comprises culturing a microorganism containing a gene encoding said enzyme in a suitable medium and under suitable conditions to express said enzyme, wherein said contacting occurs in said medium.

12. The method for producing the dipeptide according to claim 11, wherein said microorganism containing a gene encoding said enzyme is *E. coli* JM 109.

13. The method for producing the dipeptide according to claim 1, wherein said method comprises culturing a microorganism containing a gene encoding said enzyme in a suitable medium and under suitable conditions to express said enzyme, isolating the microorganism from said medium, and said contacting occurs with the isolated microorganism.

14. The method for producing the dipeptide according to claim 13, wherein said microorganism containing a gene encoding said enzyme is *E. coli* JM 109.

15. The method for producing the dipeptide according to claim 1, wherein said method comprises culturing a microorganism containing a gene encoding said enzyme in a suitable medium and under suitable conditions to express said enzyme, isolating the microorganism from said medium, treating said microorganism by a method selected from the group consisting of disruption, lysing, and freeze-drying to produce a treated microorganism cell product, and said contacting occurs with the treated microorganism cell product.

16. The method for producing the dipeptide according to claim 15, wherein said microorganism containing a gene encoding said enzyme is *E. coli* JM 109.

* * * * *